United States Patent [19]

Nishiyama et al.

[11] Patent Number: 4,546,191

[45] Date of Patent: Oct. 8, 1985

[54] TRIFLUOROMETHYL-2-PYRIDINONE OR PYRIDINTHIONE COMPOUNDS AND PROCESS FOR THE PREPARATION OF THE SAME

[75] Inventors: Ryuzo Nishiyama, Osaka; Kanichi Fujikawa, Shiga; Isao Yokomichi, Shiga; Takahiro Haga, Shiga; Kuniaki Nagatani, Shiga; Kouji Hayashi, Shiga, all of Japan

[73] Assignee: Ishihara Sangyo Kaisha Ltd., Japan

[21] Appl. No.: 131,719

[22] Filed: Mar. 19, 1980

[30] Foreign Application Priority Data

Mar. 19, 1979 [JP] Japan .................. 54-32068

[51] Int. Cl.⁴ .......................................... C07D 211/86
[52] U.S. Cl. ..................... 546/303; 546/291
[58] Field of Search ............................... 546/303, 243

[56] References Cited

U.S. PATENT DOCUMENTS

| | | | |
|---|---|---|---|
| 3,355,278 | 11/1967 | Weil et al. | 546/303 X |
| 3,634,435 | 1/1972 | Trueb et al. | 546/303 X |
| 3,682,938 | 8/1972 | Troxel et al. | 546/303 |
| 4,152,328 | 5/1979 | Nishiyama et al. | 546/302 |
| 4,184,041 | 1/1980 | Nishiyama et al. | 546/345 |
| 4,230,864 | 10/1980 | Bailey | 546/303 |
| 4,249,009 | 2/1981 | Bailey | 546/303 X |

FOREIGN PATENT DOCUMENTS

| | | |
|---|---|---|
| 862325 | 6/1978 | Belgium . |
| 865136 | 9/1978 | Belgium . |
| 865137 | 9/1978 | Belgium . |
| 50-37784 | 4/1975 | Japan . |
| 1421619 | 1/1976 | United Kingdom . |

OTHER PUBLICATIONS

Klingsberg, "Pyridine and its Derivatives", (1962) pp. 658, 659, 672, 673, Interscience Pub.
Kobayashi et al., Chemical and Pharmaceutical Bulletin, 17 (3), 510–514, (1969).

*Primary Examiner*—Joseph Paul Brust
*Attorney, Agent, or Firm*—Sughrue, Mion, Zinn, Macpeak, and Seas

[57] ABSTRACT

A trifluoromethyl-2-(thio)pyridone compound having the formula:

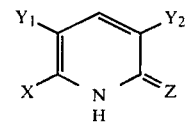

wherein X represents a hydrogen atom or a halogen atom, $Y_1$ and $Y_2$ each represents a hydrogen atom, a halogen atom or a trifluoromethyl group, and Z represents an oxygen atom or a sulfur atom, in which either $Y_1$ or $Y_2$ represents a trifluoromethyl group, and when X and $Y_2$, or X and $Y_1$ represent a hydrogen atom at the same time, then Z represents a sulfur atom, and a process for preparing the same.

2 Claims, No Drawings

TRIFLUOROMETHYL-2-PYRIDINONE OR PYRIDINTHIONE COMPOUNDS AND PROCESS FOR THE PREPARATION OF THE SAME

BACKGROUND OF THE INVENTION

1. Field of the Invention

This inventin relates to a novel trifluoromethyl-2-(thio)pyridone compound which is useful as an intermediate for medicines, agricultural chemicals, dyes, etc.

2. Description of the Prior Art

5-Trifluoromethyl-2-pyridone or 3-trifluoromethyl-2-pyridone compounds having a chemical structure analogous to the trifluoromethyl-2-pyridinone or pyridinthione compounds of this invention have been known by, for example, British Pat. No. 1,421,619 or *Chemical and Pharmaceutical Bulletin*, 17 (3), pp 510–514 (1969). However, the compounds of this invention are not easy to prepare on an industrial scale.

SUMMARY OF THE INVENTION

A primary object of the present invention is to provide a trifluoromethyl-2-pyridinone or pyridinthione compound having the formula (I):

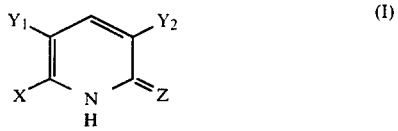

wherein X represents a hydrogen atom or a halogen atom, $Y_1$ and $Y_2$ each represents a hydrogen atom, a halogen atom or a trifluoromethyl group, and Z represents an oxygen atom or a sulfur atom, in which either $Y_1$ or $Y_2$ represents a trifluoromethyl group, and when X and $Y_2$, or X and $Y_1$ represent a hydrogen atom at the same time, then Z represents a sulfur atom.

Another object of the present invention is to provide a process for preparing the compound of the formula (I).

DETAILED DESCRIPTION OF THE INVENTION

The trifluoromethyl-2-(thio)pyridone compounds of the formula (I) of this invention can be prepared by the following method.

Reaction Scheme (A)

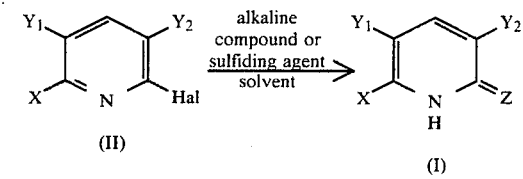

In the above reaction scheme (A), X, $Y_1$, $Y_2$ and Z are the same as defined hereinbefore, and Hal represents a halogen atom. Suitable examples of the halogen atom used for X, $Y_1$, $Y_2$ and Hal include a chlorine atom, a bromine atom, a fluorine atom, etc.

The above-described reaction is generally carried out in the presence of a solvent. Suitable examples of the solvent used include an alcohol such as methanol, ethanol, t-butanol, etc., a polar aprotic solvent such as dimethyl sulfoxide, dimethylformamide, etc., water and the like. Suitable examples of the alkaline compound which can be used include alkali metal hydroxides such as sodium hydroxide, potassium hydroxide, etc., alkaline earth metal hydroxides such as calcium hydroxide, magnesium hydroxide, etc., and the like. A suitable amount of the alkaline compound generally ranges from 1 to 2.2 mols per mol of the compound of the formula (II). Suitable examples of the sulfiding agent which can be used include thiourea, sodium hydrosulfide, sodium sulfide, sodium thiosulfate, sodium N,N-dimethyldithiocarbamate and the like. A suitable amount of the sulfiding agent generally ranges from 1 to 2.2 mols per mol of the compound of the formula (II). The reaction is generally carried out at temperatures ranging from 50° C. to the reflux temperature, preferably from 80° to 100° C. for a period of time ranging from 0.1 to 10 hours. It is desirable from the industrial viewpoint to use t-butanol for the solvent, potassium hydroxide for the alkaline compound, and sodium hydrosulfide or sodium sulfide for the sulfiding agent, respectively.

The above-described reaction is generally carried out by reacting the compound of the formula (II) with a solution of the alkaline compound or sulfiding agent dissolved in the solvent. After the reaction completes, the reaction product is rendered acidic with an acid to thereby obtain a precipitate which is then filtered to obtain a desired compound of this invention.

Further, a compound having the formula (IV) hereinafter described can be prepared in accordance with the following reaction scheme (B) in which a compound having the formula (III) also hereinafter described is reacted with a halogenating agent in the presence of a solvent.

Reaction Scheme (B)

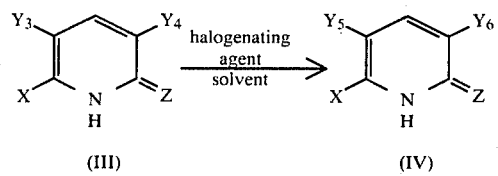

In the above reaction scheme (B), X and Z are the same as defined hereinbefore, $Y_3$ and $Y_4$ each represents a hydrogen atom or a trifluoromethyl group in which either $Y_3$ or $Y_4$ represents a trifluoromethyl group, and $Y_5$ and $Y_6$ each represents a halogen atom or a trifluoromethyl group in which either $Y_5$ or $Y_6$ represents a trifluoromethyl group. Suitable examples of the halogen atom used for $Y_5$ and $Y_6$ include a chlorine atom, a bromine atom, etc.

This reaction is generally carried out in the presence of a solvent. Suitable examples of the solvent used include a halogenated hydrocarbon such as carbon tetrachloride, chloroform, etc., a polar aprotic solvent such as dimethyl sulfoxide, dimethylformamide, etc., acetic acid, carbon disulfide, water and the like.

As the halogenating agent which can be used, it is to be avoided to use strong halogenating agents such that they likely substitute with a halogen atom the hydroxy group at the 2-position on the pyridine nucleus. Suitable examples of the halogenating agent include a chlorinating agent such as chlorine gas, t-butyl hypochlorite, etc., and a brominating agent such as bromine, N-bromosuccinimide, a dioxane-bromine complex, etc. A suitable amount of the halogenating agent generally ranges from 1 to 1.5 mols per mol of the compound of the formula (III). The reaction is carried out at a temperature ranging from 0° to 100° C., preferably from 20° to 60° C. for a period of time ranging from 0.5 to 10 hours. It is desirable from the industrial viewpoint to use a chlorine gas or bromine as the halogenating agent.

The reaction shown in the reaction scheme (B) is generally carried out by blowing into or adding to a solution of the compound of the formula (III) dissolved in the solvent the halogenating agent. After completion of the reaction, the solvent is distilled off from the reaction product and optionally, a purification treatment is carried out to obtain a halogen-substituted trifluoromethyl-2-pyridinone or pyridinthione of the formula (IV).

Almost all of the starting materials used in the above-described reaction schemes are a known compound. For example, 2-chloro-5-trifluoromethylpyridine and 5-trifluoromethyl-2-pyridone are disclosed in British Pat. No. 1,421,619, 3-trifluoromethyl-2-pyridone is described in *Chemical and Pharmaceutical Bulletin*, 17 (3), pp 510–514 (1969), and 2,3-dichloro-5-trifluoromethylpyridine and 2-chloro-3-bromo-5-trifluoromethylpyridine are disclosed in Belgian Pat. Nos. 865,136 and 865,137, respectively. Furthermore, 2,6-dichloro-3-trifluoromethylpyridine is disclosed in Japanese Patent Application (OPI) No. 37784/75, and the compounds of the formula (II) wherein $Y_1$ represents a trifluoromethyl group are disclosed in Belgian Pat. No. 862,325. Of the compounds of the formula (II), unknown compounds can be prepared in accordance with the methods described in the above-cited references.

Some typical compounds of the present invention are listed below.

3-Chloro-5-trifluoromethyl-2-pyridone—m.p. 165°–166° C.
5-Trifluoromethyl-2-thiopyridone—m.p. 147°–150° C.
3-Bromo-5-trifluoromethyl-2-pyridone—m.p. 162°–165° C.
3-Chloro-5-trifluoromethyl-2-thiopyridone—m.p. 125°–128° C.
3,6-Dichloro-5-trifluoromethyl-2-pyridone—m.p. 129°–131° C.
5,6-Dichloro-3-trifluoromethyl-2-pyridone—m.p. 163°–165° C.
6-Chloro-5-trifluoromethyl-2-pyridone—m.p. 143°–145° C.
6-Chloro-3-trifluoromethyl-2-pyridone—m.p. 87°–89° C.
5-Bromo-3-trifluoromethyl-2-pyridone—m.p. 166°–170° C.

The compounds of the present invention can be introduced into N-benzoyl-N'-[4-(5-trifluoromethylpyridyl-2-oxy)phenyl]urea compounds by, for example, condensing with halogenated nitrobenzenes to form 4-(5-trifluoromethylpyridyl-2-oxy)nitrobenzenes, reducing to 4-(5-trifluoromethylpyridyl-2-oxy)anilines and reacting with benzoylisocyanates. More specifically, 3-chloro-5-trifluoromethyl-2-pyridone of this invention is once converted into its silver salt in accordance with the method described in *Justus Liebigs Annalen Der Chemie*, 484, pp 56 (1930). The silver salt is condensed with 3,4,5-trichloronitrobenzene and reduced to form 3,5-dichloro-4-(3-chloro-5-trifluoromethylpyridyl-2-oxy)aniline which is then reacted with 2,6-difluorobenzoylisocyanate to thereby form N-(2,6-difluorobenzoyl)-N'-[3,5-dichloro-4-(3-chloro-5-trifluoromethylpyridyl-2-oxy)phenyl]urea. The thus formed urea compound exhibits an excellent activity as an active ingredient for insecticides, and is effective in controlling various injurious insects. For example, it has been confirmed that when 2nd to 3rd instar larvae of diamond-back moth (*Plutella xylostella*) was released on pieces of leaves of cabbage which had preliminarily been immersed in a 100 ppm aqueous dispersion of the above-described urea compound and air-dried, the alive and dead was evaluated 8 days later to thereby obtain a mortality rate of 100%.

The following Examples are given to illustrate the preparation of some typical compounds of this invention, but they are not to be construed as limiting the present invention.

EXAMPLE 1

Preparation of 3-Chloro-5-trifluoromethyl-2-pyridone

[A] 0.2 g of 5-trifluoromethyl-2-pyridone was dissolved in 20 ml of chloroform, and chlorine gas was pressed through the solution at 50° C. for 1 hour while stirring. After completion of the reaction, the chloroform was distilled off, and recrystallization was performed from a mixed solvent of toluene and n-hexane to obtain 0.15 g of the titled compound having a melting point of 144° to 147° C. The recrystallization was further repeated to obtain 0.09 g of the titled compound having a melting point of 165° to 166° C.

[B] 4 g of 2,3-dichloro-5-trifluoromethylpyridine was added to an aqueous solution of 2.4 g of sodium hydroxide dissolved in 12.5 ml of water, and 12.5 ml of dimethyl sulfoxide was further added thereto. The solution was reacted at 110° C. for 1 hour while stirring. After completion of the reaction, the reaction product was allowed to cool and made acidic with concentrated hydrochloric acid to obtain a precipitate. The thus obtained precipitate was collected by filtration to obtain 2.5 g of the titled compound.

EXAMPLE 2

Preparation of 5-Trifluoromethyl-2-thiopyridone 4 g of 2-chloro-5-trifluoromethylpyridine and 1.67 g of thiourea were dissolved in 30 ml of ethanol, and the solution was reacted for 3 hours under the reflux condition. Thereafter, 1.23 g of an aqueous solution of potassium hydroxide was gradually added to the reaction solution which was then reacted for an additional one hour under the reflux condition. After the reaction completed, the reaction product was allowed to cool and poured into a dilute alkali aqueous solution. The resulting product was washed with methylene chloride and made acidic with acetic acid. Then, the product was extracted with methylene chloride, and the extraction layer was washed with water and dried over anhydrous sodium sulfate. The methylene chloride was distilled off to obtain 2.1 g of the titled compound having a melting point of 147° to 150° C.

EXAMPLE 3

Preparation of 3-Bromo-5-trifluoromethyl-2-pyridone 0.4 g of 5-trifluoromethyl-2-pyridone was dissolved in 10 ml of acetic acid, and 0.4 g of bromine was added to the solution which was subsequently reacted for 4 hours while stirring. After completion of the reaction, the acetic acid was distilled off, and recrystallization was carried out from a mixed solvent of methylene chloride and n-hexane to obtain 0.45 g of the titled compound having a melting point of 162° to 165° C.

EXAMPLE 4

Preparation of 3-Chloro-5-trifluoromethyl-2-thiopyridone

The same procedure as in Example 2 was followed except that 4.75 g of 2,3-dichloro-5-trifluoromethylpyridine was used in place of 4 g of 2-chloro-5-trifluoromethylpyridine to obtain 1.9 g of the titled compound having a melting point of 125° to 128° C.

EXAMPLE 5

Preparation of 3-Chloro-5-trifluoromethyl-2-pyridone 4.5 g of 2,3-dichloro-5-trifluoromethylpyridine was added to a solution of 2.7 g of potassium hydroxide dissolved in 40 ml of t-butanol, and the mixture was reacted at the reflux temperature for one hour while stirring. After completion of the reaction, the reaction product was allowed to cool and made acidic with concentrated hydrochloric acid. The contents were concentrated under reduced pressure to obtain a solid which was then purified to obtain 3.1 g of the titled compound having a melting point of 165° to 166° C.

Further, 60 g of a silver salt of 3-chloro-5-trifluoromethyl-2-pyridone prepared in Example 5, the silver salt having been prepared in the conventional manner, was reacted with 46.8 g of 3,4,5-trichloronitrobenzene in dimethoxyethane for 24 hours under the reflux condition while stirring. After completion of the reaction, the reaction product was treated in the conventional manner. The thus treated product was passed through a silica gel column (eluent: toluene) to thereby separate 15.6 g of 3-chloro-2-(2,6-dichloro-4-nitrophenoxy)-5-trifluoromethylpyridine. This product was then reduced in ethanol in the presence of 29.5 g of stannous chloride in the conventional manner to obtain 7.5 g of 3,5-dichloro-4-(3-chloro-5-trifluoromethylpyridyl-2-oxy)aniline having a melting point of 150° to 153° C.

A solution was prepared by dissolving 7.2 g of 3,5-dichloro-4-(3-chloro-5-trifluoromethylpyridyl-2-oxy)aniline in 30 ml of dioxane. A solution prepared by dissolving 3.6 g of 2,6-difluorobenzoylisocyanate in 10 ml of dioxane was dropwise added to the former solution while stirring, and the reaction was carried out at room temperature (i.e., about 20°–30° C.) for 1 hour. After cooling the reaction product, a precipitate obtained by adding water to the product was filtered and washed with n-hexane and then, recrystallized from dioxane to obtain 10.1 g of N-(2,6-difluorobenzoyl)-N'-[3,5-dichloro-4-(3-chloro-5-trifluoromethylpyridyl-2-oxy)phenyl]urea having a melting point of 217° to 220° C.

EXAMPLE 6

Preparation of 3-Chloro-5-trifluoromethyl-2-thiopyridone 2.2 g of 2,3-dichloro-5-trifluoromethylpyridine and 1.1 g of sodium sulfide were dissolved in 30 ml of t-butanol, and the solution was reacted at the reflux temperature for 5 hours. Thereafter, 0.9 g of an aqueous solution of potassium hydroxide was gradually added thereto, and the mixture was reacted for an additional one hour under the reflux condition. After completion of the reaction, the reaction product was allowed to cool and poured into a dilute alkali aqueous solution followed by washing with methylene chloride and then making acidic with acetic acid. Then, the product was extracted with methylene chloride, and the extraction layer was washed with water and dried over anhydrous sodium sulfate. The methylene chloride was distilled off to obtain 0.8 g of the titled compound having a melting point of 125° to 128° C.

EXAMPLE 7

Preparation of 3,6-Dichloro-5-trifluoromethyl-2-pyridone and 5,6-Dichloro-3-trifluoromethyl-2-pyridone To a solution of 2.7 g of potassium hydroxide dissolved in 37 ml of t-butanol was added 6.0 g of 2,3,6-trichloro-5-trifluoromethylpyridine, and the solution was reacted at 80° C. for 3 hours while stirring. After completion of the reaction, the reaction product was allowed to cool and made acidic with concentrated hydrochloric acid. The solvent was distilled off under reduced pressure, and the residue was extracted with methylene chloride. The methylene chloride solution was washed with water and dried over anhydrous sodium sulfate. The methylene chloride was distilled off under reduced pressure, and the resulting residue was passed through a silica gel column (eluent: an n-hexane-ethyl acetate (3:1 by weight) mixture) to obtain 1.5 g of 3,6-dichloro-5-trifluoromethyl-2-pyridone having a melting point of 129° to 131° C. and 0.8 g of 5,6-dichloro-3-trifluoromethyl-2-pyridone having a melting point of 163° to 165° C., respectively.

While the invention has been described in detail and with reference to specific embodiments thereof, it will be apparent to one skilled in the art that various changes and modifications can be made therein without departing from the spirit and scope thereof.

What is claimed is:

1. 3-chloro-5-trifluoromethyl-2-pyridone.
2. 3-bromo-5-trifluoromethyl-2-pyridone.

* * * * *